US010406081B2

(12) United States Patent
Mundschau et al.

(10) Patent No.: US 10,406,081 B2
(45) Date of Patent: Sep. 10, 2019

(54) MULTIFUNCTIONAL BASE EMULSION

(71) Applicant: KIMBERLY-CLARK WORLDWIDE, INC., Neenah, WI (US)

(72) Inventors: Stacy A. Mundschau, Weyauwega, WI (US); YoenJung Lee, Yongin-Si (KR); Scott W. Wenzel, Neenah, WI (US); Jeffery R. Seidling, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 15/533,812

(22) PCT Filed: Dec. 29, 2015

(86) PCT No.: PCT/US2015/067797
§ 371 (c)(1),
(2) Date: Jun. 7, 2017

(87) PCT Pub. No.: WO2016/109488
PCT Pub. Date: Jul. 7, 2016

(65) Prior Publication Data
US 2017/0360659 A1 Dec. 21, 2017

Related U.S. Application Data

(60) Provisional application No. 62/097,260, filed on Dec. 29, 2014.

(51) Int. Cl.
*A61K 8/06* (2006.01)
*A61K 8/19* (2006.01)
*A61K 8/81* (2006.01)
*A61K 8/89* (2006.01)
*A61K 8/891* (2006.01)
*A61K 8/92* (2006.01)
*A61Q 19/00* (2006.01)
*A61K 8/25* (2006.01)
*A61K 8/41* (2006.01)
*A61K 8/894* (2006.01)
*A61K 8/04* (2006.01)

(52) U.S. Cl.
CPC ............. *A61K 8/064* (2013.01); *A61K 8/046* (2013.01); *A61K 8/25* (2013.01); *A61K 8/416* (2013.01); *A61K 8/891* (2013.01); *A61K 8/894* (2013.01); *A61Q 19/00* (2013.01)

(58) Field of Classification Search
None
See application file for complete search history.

(56) References Cited

U.S. PATENT DOCUMENTS

| | | |
|---|---|---|
| 3,856,941 A | 12/1974 | Turner |
| 4,350,605 A | 9/1982 | Hughett |
| 4,774,079 A | 9/1988 | Shin et al. |
| 4,801,447 A | 1/1989 | Gum |
| 4,983,418 A | 1/1991 | Murphy et al. |
| 5,085,855 A | 2/1992 | Shore |
| 5,876,702 A * | 3/1999 | Gers-Barlag .......... A61K 8/066 424/400 |
| 6,042,815 A | 3/2000 | Kellner et al. |
| 6,103,250 A | 8/2000 | Brieva et al. |
| 6,242,396 B1 | 6/2001 | Guillou et al. |
| 6,261,543 B1 | 7/2001 | Fletcher et al. |
| 6,419,935 B1 | 7/2002 | Gueret |
| 6,419,938 B1 | 7/2002 | Riedel et al. |
| 6,492,326 B1 | 12/2002 | Robinson et al. |
| 6,685,952 B1 | 2/2004 | Ma et al. |
| 6,878,805 B2 | 4/2005 | Manoharan et al. |
| 6,974,799 B2 | 12/2005 | Lintner |
| 7,157,077 B2 | 1/2007 | Shen |
| 7,282,197 B2 | 10/2007 | Diec et al. |
| 7,326,409 B2 | 2/2008 | Lemoine et al. |
| 7,566,464 B2 | 7/2009 | Belfer |
| 7,811,594 B2 | 10/2010 | Schreiber et al. |
| 7,863,417 B2 | 1/2011 | Ziegler et al. |
| 8,182,828 B2 | 5/2012 | Omura et al. |
| 8,575,106 B2 | 11/2013 | Santhanam et al. |
| 8,597,622 B2 | 12/2013 | Lemoine et al. |
| 8,697,656 B2 | 4/2014 | Fournial et al. |

(Continued)

FOREIGN PATENT DOCUMENTS

| | | |
|---|---|---|
| DE | 10140637 A1 | 3/2003 |
| EP | 0717981 B1 | 2/2000 |
| EP | 1714638 A1 | 10/2006 |
| EP | 2143418 A1 | 1/2010 |
| GB | 2069333 A | 8/1981 |
| JP | 4573690 B2 | 11/2010 |
| KR | 10-1355051 B1 | 1/2014 |
| WO | WO 2002/047624 A1 | 6/2002 |
| WO | WO 2004/112739 A1 | 12/2004 |
| WO | WO 2006/028311 A1 | 3/2006 |
| WO | WO 2007/046097 A2 | 4/2007 |
| WO | WO 2012/062755 A2 | 5/2012 |
| WO | WO 2012/174096 A2 | 12/2012 |
| WO | WO 2015/066194 A1 | 5/2015 |
| WO | WO15163838 A1 | 10/2015 |
| WO | WO15170063 A1 | 11/2015 |

OTHER PUBLICATIONS

Siltech, Technical Data Sheet for Silube J1015-O-812, May 2013, 1 page.*

(Continued)

*Primary Examiner* — Brian Gulledge
(74) *Attorney, Agent, or Firm* — Kimberly-Clark Worldwide, Inc.

(57) ABSTRACT

Multi-functional base emulsions that can be used to form a variety of cosmetic compositions are disclosed. In one aspect, a cosmetic emulsion can include a water phase including about 10% to about 67.5% water by total weight of the cosmetic emulsion. The cosmetic emulsion can also include an oil phase that includes (a) stearalkonium hectorite, and (b) a silicone alkyl polyether selected from the group consisting of: PEG/PPG-18/18 dimethicone, PEG/PPG-20/15 dimethicone, and Lauryl PEG/PPG-18/18 dimethicone.

9 Claims, No Drawings

(56) References Cited

U.S. PATENT DOCUMENTS

| | | |
|---|---|---|
| 8,741,357 B2 | 6/2014 | Lintner et al. |
| 8,758,833 B2 | 6/2014 | Garnier et al. |
| 8,815,814 B2 | 8/2014 | Bardey et al. |
| 8,871,717 B2 | 10/2014 | Osborne |
| 10,111,824 B2 | 10/2018 | Lee et al. |
| 2002/0155080 A1 | 10/2002 | Glenn et al. |
| 2003/0049218 A1 | 3/2003 | Patel et al. |
| 2003/0206934 A1 | 11/2003 | Riedel et al. |
| 2004/0013631 A1 | 1/2004 | Harichian et al. |
| 2004/0241105 A1* | 12/2004 | Riedel .................. A61K 8/046 424/47 |
| 2005/0002973 A1 | 1/2005 | Johansson et al. |
| 2005/0053568 A1 | 3/2005 | Aubrun-Sonneville et al. |
| 2005/0058669 A1 | 3/2005 | Krzysik et al. |
| 2005/0100585 A1 | 5/2005 | Patel et al. |
| 2005/0152931 A1 | 7/2005 | SaNogueira et al. |
| 2006/0018855 A1 | 1/2006 | Batista et al. |
| 2006/0045894 A1 | 3/2006 | Brown et al. |
| 2006/0140899 A1 | 6/2006 | Koenig et al. |
| 2007/0218025 A1 | 9/2007 | Schulz et al. |
| 2007/0292359 A1 | 12/2007 | Friedman et al. |
| 2008/0038219 A1 | 2/2008 | Mosbaugh et al. |
| 2008/0253973 A1 | 10/2008 | Tamarkin et al. |
| 2009/0010972 A1 | 1/2009 | Modafari et al. |
| 2009/0047226 A1 | 2/2009 | Teckenbrock et al. |
| 2009/0054346 A1 | 2/2009 | Takiguchi et al. |
| 2009/0269374 A1 | 10/2009 | Lee et al. |
| 2010/0008957 A1 | 1/2010 | Mundschau et al. |
| 2010/0008958 A1 | 1/2010 | Mundschau et al. |
| 2011/0010817 A1 | 1/2011 | Theberge et al. |
| 2011/0229536 A1 | 9/2011 | Kvitnitsky et al. |
| 2012/0058140 A1 | 3/2012 | Ceccoli et al. |
| 2012/0076842 A1 | 3/2012 | Fournial et al. |
| 2012/0095115 A1 | 4/2012 | Kawa et al. |
| 2012/0100197 A1 | 4/2012 | Kawa et al. |
| 2012/0128601 A1 | 5/2012 | Behler et al. |
| 2012/0129786 A1 | 5/2012 | Heidl et al. |
| 2012/0258055 A1* | 10/2012 | Gray ..................... A61K 8/26 424/59 |
| 2012/0277313 A1 | 11/2012 | Kwon et al. |
| 2013/0164238 A1 | 6/2013 | Banowski et al. |
| 2013/0336903 A1 | 12/2013 | Fernandez Prieto et al. |
| 2014/0004166 A1 | 1/2014 | Cunningham et al. |

OTHER PUBLICATIONS

Co-pending U.S. Appl. No. 16/066,258, filed Jun. 26, 2018, by Lee et al. for "Cosmetic Formulations".

\* cited by examiner

MULTIFUNCTIONAL BASE EMULSION

TECHNICAL FIELD

The present disclosure relates to an emulsion that can be used to formulate a multitude of different cosmetic compositions. The stable, largely anhydrous emulsion is a water-in-oil emulsion which is sprayable even at relatively low water content.

BACKGROUND OF THE DISCLOSURE

Manufacturers of personal care and cosmetic products typically use a variety of emulsions. This requires a certain supply chain and manufacturing complexity. Using a common formulation to create a variety of products ranging from lotions to creams would greatly simplify the manufacturing supply chain and reduce overall manufacturing costs. However, there are limitations to the extent which a formulation can be used in a variety of products because of instability.

What is needed is a common base emulsion that can be used to make a variety of cosmetics. It is desirable to have a common base emulsion that is sprayable. Further, it is desirable to have a common base emulsion that is largely anhydrous, yet stable.

SUMMARY OF THE DISCLOSURE

In one embodiment, a cosmetic emulsion can include a water phase and an oil phase. The water phase can include about 10% to about 67.5% water by total weight of the cosmetic emulsion. The oil phase can include: (a) stearalkonium hectorite; and (b) a silicone alkyl polyether selected from the group consisting of: PEG/PPG-18/18 dimethicone, PEG/PPG-20/15 dimethicone, and Lauryl PEG/PPG-18/18 dimethicone.

In another embodiment, a cosmetic emulsion can include a water phase and an oil phase. The water phase can include about 10% to about 45% water by total weight of the cosmetic emulsion. The oil phase can include (a) stearalkonium hectorite; and (b) a silicone alkyl polyether selected from the group consisting of: PEG/PPG-18/18 dimethicone, PEG/PPG-20/15 dimethicone, and Lauryl PEG/PPG-18/18 dimethicone. The cosmetic emulsion can be sprayable.

In yet another embodiment, a cosmetic emulsion can be in a form of a lotion or a cream. The cosmetic emulsion can include a water phase and an oil phase. The water phase can include about 45% to about 67.5% water by total weight of the emulsion. The oil phase can include (a) stearalkonium hectorite; and (b) a silicone alkyl polyether selected from the group consisting of: PEG/PPG-18/18 dimethicone, PEG/PPG-20/15 dimethicone, and Lauryl PEG/PPG-18/18 dimethicone.

DETAILED DESCRIPTION OF THE DISCLOSURE

The present disclosure relates to a novel emulsion that can be used to manufacture a wide variety of product forms ranging from sprays to lotions to creams. Each product form has its own benefit to consumers. One of several advantages of this base emulsion is that manufacturers of cosmetic products are no longer forced to differentiate their products by merely changing minor ingredients. They instead can afford to truly innovate to create new and very different formulations. In addition, having a common base emulsion capable of being used in such a wide variety of product forms will greatly reduce supply chain complexity and manufacturing costs. Other advantages will become apparent in the following disclosure.

In some embodiments, the formulation of the present disclosure can be "sprayable." As used herein, the term "sprayable" refers to the ability to spray the formulation with a hand-pump spray bottle, a hand-squeeze spray bottle, pressurized aerosol cans, or similar devices. The formulation of the present disclosure can be dispensed through a hand-held spray dispenser by pressing a dispensing button to spray the formulation onto the skin. For the purposes of this disclosure, "sprayable" emulsions were those that were able to dispense through the Calmar Mark VI® dispenser commercially produced by MeadWestvaco Corporation. The specifications of the spray head of this dispenser are a 20 mm cap with 410 thread, an overall spray volume of 0.16 cc, a spray diameter of 0.057 inches and a dip tube of 2.75 inches. The formulation was loaded into a 2 oz. Boston Round bottle available from Poly-Tainer Inc. (20/410 thread). If the formulation was able to disperse from the package within 10 pumps, the formulation is deemed as "sprayable," as the term is used herein. Other than the pressure applied from the manual depression of the pump, no other pressure is present within the packaging (i.e. aerosolized, pressurized CO2, etc). In some embodiments, preferred formulations produce a v-shaped pattern of the formulation upon spraying that give droplets upon the skin. Of course, it is contemplated that other conventional spray dispenser mechanism can be used to dispense the skin protectant formulation, including, but not limited to, aerosol or pressurized propellant dispensers, motor driven pump dispensers, and other dispensers using manual spray pump mechanisms. In some embodiments, an emulsion can be sprayable and have a viscosity of about 1 to about 15,000 cps, or about 1 to about 10,000 cps, or about 500 to 8,000 cps.

In a preferred embodiment, the skin protectant formulation of the present disclosure may be utilized with a continuous spray dispenser. Continuous spray, or continuously sprayable, technology is meant to indicate that the formulation provides any angle spraying and uniform coverage. An example of a continuous spray dispenser would include a flexible, expandable container adapted to receive the skin protectant formulation. The flexible container is removable surrounded by a rigid exterior housing or canister, which is provided with an air-tight seal. The canister is sealed prior to filling the flexible container with the skin protectant formulation, so that air is trapped within the canister in the volume unoccupied by the flexible container. When the flexible container is filled with the skin protectant formulation, the container expands, thereby compressing the air within the canister. While maintaining complete separation from the skin protectant formulation, this compressed air acts as a propellant. The compressed air then acts against the flexible container to uniformly propel the skin protectant formulation from the container. In this example, there is no need to pump the spray like conventional spray dispensers to distribute the formulation onto skin. This is advantageous in limiting pain for those with limited dexterity or arthritis.

In another exemplary continuous spray dispenser, the container may include a pump that is integral with the cap on the dispenser. In this example, the air is compressed in the canister not when sealing the canister, but by pumping air into the canister to provide compressed air as a propellant. The compressed air added by a consumer then acts against the flexible container to uniformly propel the skin protectant formulation out of the container.

Continuous spray technology is well known in the art. Suitable commercially available continuous spray dispensers for use with the skin protectant formulation can include, for example, the 12HS Dry Spray Dispenser commercially available from Rexam Airspray, or the bag-on-valve dispenser commercially available from ColepCCL.

The term "stable" is defined as an emulsion which remains uniform in appearance with no signs of separation of the oil- and water-soluble ingredients after three months at 40° C.

The primary components of one base emulsion of the present disclosure are a water phase including about 10% to about 67.5% by weight water; and an oil phase that includes (a) a silicone alkyl polyether selected from the group consisting of: PEG/PPG-18/18 dimethicone, PEG/PPG-20/15 dimethicone, and Lauryl PEG/PPG-18/18 dimethicone, functioning as an emulsifying surfactant, and (b) stearalkonium hectorite functioning as a thickener. In a preferred embodiment, the oil phase of the base emulsion can further include a silicone-5 based oils, including dimethicone (10 cst). Lauryl PEG/PPG-18/18 dimethicone is available from Siltech Corporation, Toronto, Ontario, Canada, under SILUBE J1015 O-812. Stearalkonium hectorite is available from Elementis Specialities of London, England as BENTONE Gel® CAO.

In one aspect of the disclosure is a sprayable emulsion that includes a water phase including about 10% to about 45% by weight water; and an oil phase that includes (a) a silicone alkyl polyether selected from the group consisting of: PEG/PPG-18/18 dimethicone, PEG/PPG-20/15 dimethicone, and Lauryl PEG/PPG-18/18 dimethicone and (b) stearalkonium hectorite.

In a second aspect of the disclosure is a non-sprayable emulsion that includes a water phase including about 45% to about 67.5% by weight water and an oil phase including (a) a silicone alkyl polyether selected from the group consisting of: PEG/PPG-18/18 dimethicone, PEG/PPG-20/15 dimethicone, and Lauryl PEG/PPG-18/18 Dimethicone and (b) stearalkonium hectorite. The emulsion is in the form of a lotion or heavy cream. Here, a particular ratio of the silicone alkyl polyether and stearalkonium hectorite can preferably be at least 2:1 for enhanced stability.

Optional Ingredients:

The emulsions of the present disclosure may additionally include adjunct ingredients conventionally found in pharmaceutical compositions in an established fashion and at established levels. For example, the anti-adherent compositions may comprise additional compatible pharmaceutically active and compatible materials for combination therapy, such as antioxidants, antiparasitic agents, antipruritics, antifungals, antiseptic actives, biological actives, astringents, keratolytic actives, local anaesthetics, anti-stinging agents, anti-reddening agents, skin soothing agents, external analgesics, film formers, skin exfoliating agents, sunscreens, and combinations thereof.

Other suitable additives that may be included in the emulsions of the present disclosure include compatible colorants, deodorants, lubricants, skin conditioning agents, skin protectants and skin benefit agents (e.g., aloe vera and tocopheryl acetate), solvents, solubilizing agents, pH adjusting ingredients (a suitable pH range of the compositions can be from about 3.5 to about 8), chelators, dyes and/or pigments, and combinations thereof.

Another component that may be suitable for addition to the emulsions is a fragrance. Any compatible fragrance may be used. Typically, the fragrance is present in an amount from about 0% (by total weight of the emulsion) to about 5% (by total weight of the emulsion), and more typically from about 0.01% (by total weight of the emulsion) to about 3% (by total weight of the emulsion). In one desirable embodiment, the fragrance will have a clean, fresh and/or neutral scent to create an appealing delivery vehicle for the end consumer.

Sunscreens that may be present in the emulsions include ethylhexyl methoxycinnamate, avobenzone, octocrylene, benzophenone-4, phenylbenzimidazole sulfonic acid, homosalate, oxybenzone, benzophenone-3, ethylhexyl salicylate, titanium dioxide, zinc oxide and mixtures thereof.

Antimicrobial agents may be added to the emulsions. For example, suitable antimicrobials include biocides such as a short-chain alcohol, benzoalkonium chloride ("BAC"), 5 didecyl dimethyl ammonium chloride ("DDAC"), and zeolite ("CWT-A"). Other possible antimicrobial agents include: isothiazolone, alkyl dimethyl ammonium chloride, a triazine, 2-thiocyanomethylthio benzothiazol, methylene bis thiocyanate, acrolein, dodecylguanidine hydrochloride, a chlorophenol, a quaternary ammonium salt, gluteraldehyde, a dithiocarbamate, 2-mercatobenzothiazole, para-chlorometa10 xylenol, silver, chlorohexidine, polyhexamthylene biguanide, a n-halamine, triclosan, a phospholipid, an alpha hydroxyl acid, 2,2-dibromo-3-nitrilopropionamide, 2-bromo-2-nitro-1,3-propanediol, farnesol, iodine, bromine, hydrogen peroxide, chlorine dioxide, a botanical oil, a botanical extract, benzalkonium chloride, chlorine, sodium hypochlorite, or combinations thereof.

When present, the amount of the antimicrobial agent in the compositions is in an amount between about 0.01% to about 5% (by total weight of the emulsion), or in some embodiments between about 0.05% to about 3% (by total weight of the emulsion).

The emulsions may include various preservatives to increase shelf life. Some suitable preservatives that may be used in the present disclosure include, but are not limited to: phenoxyethanol, capryl glycol, glyceryl caprylate, sorbic acid, gallic acid, KATHON™ CG®, which is a mixture of methylchloroisothiazolinone and methylisothiazolinone, (available from Rohm & Haas Company, Philadelphia, Pa.); DMDM hydantoin (e.g., GLYDANT™, available from Lonza, Inc., Fair Lawn, N.J.); EDTA and salts thereof; iodopropynyl butylcarbamate; benzoic esters (parabens), such as methylparaben, propylparaben, butylparaben, ethylparaben, isopropylparaben, isobutylparaben, benzylparaben, sodium methylparaben, and sodium propylparaben; 2-bromo-2-nitropropane-1,3-diol; benzoic acid; and the like. Other suitable preservatives include those sold by Sutton Labs Inc., Chatham, N.J., such as "GERMALL® 115" (imidazolidinyl urea), "GERMALL® II" (diazolidinyl urea), and "GERMALL® PLUS" (diazolidinyl urea and iodopropynyl butylcarbonate). The amount of the preservative in the emulsions is dependent on the relative amounts of other components present within the composition. For example, in some embodiments, the preservative is present in the compositions in an amount between about 0.001% to about 5% (by total weight of the emulsion), in some embodiments between about 0.01% to about 3% (by total weight of the emulsion), and in some embodiments, between about 0.05% to about 1.0% (by total weight of the emulsion).

The emulsions may contain phase change materials (PCM) which may serve as a heat sink as body temperatures rise. The inclusion of PCMs may be particularly useful for menopausal women as the rise in skin temperature associated with a hot flash would cause the PCMs to melt to provide a controlled cooling effect to prevent sweating episodes that typically follow a hot flash. Particularly useful PCMs include a combination of Lauric and Myristic Acid, which, when blended together at the proper ratio, produce a melt point near 36° C., which exemplifies the skin temperature of a woman having a hot flash. The ratios of Lauric acid and either Steric or Myristic acid that are necessary to produce a specific melting point has been determined by Karaipekli et al. and published within Energy Sources (Part A: Recovery, Utilization & Environmental Effects; 30; 13-16, p 1248-1258, 2008). In one embodiment, approximately a combination of 72% Lauric Acid and 28% Steric Acid or 68% Lauric Acid and 32% Myristic produced a mixture with the desired melt temperature. Other PCMs can include, but are not limited to, hydrocarbons, waxes, oils, natural butters, fatty acids, fatty acid esters, dibasic acids, dibasic esters, 1-halides, primary alcohols, aromatic compounds, anhydrides, ethylene carbonate, polyhydric alcohols, tricaprin, parrafin, nonadecane, octadecane, stearyl heptanoate, lauryl lactate, lauryl alcohol, capric acid, caprylic acid, cetyl babassuate, *Mangifera indica* (mango) seed butter, *Theobroma cacao* (cocoa) seed butter, *Butyrospermum parkii* butter, Di-C.sub.12-15Alkyl Fumarate, stearyl caprylate, cetyl lactate, cetyl acetate, C.sub.24-28 alkyl methicone, glyceryl dilaurate, stearamidopropyl PG-dimonium chloride phosphate, jojoba esters, and any combinations thereof.

The emulsions may further include water soluble ingredients known to bind fecal proteases associated with diaper rash. Examples of such ingredients include bentonite, hectorite, magnesium aluminum silicate, zinc chloride, and zinc sulfate. The exact use level of these ingredients largely depends on the specific application but generally is no greater than 5% w/w.

The emulsions can further include salts, including, but not limited to, aluminum salts. In some embodiments, the aluminum salt can range from 0.25% to 1.0% aluminum content. Exemplary aluminum salts can include: Ammonium and Potassium Alum, Aluminum Triphosphate, Sodium aluminum Phosphate, Aldioxa, Aluminum Stearate, Aluminum Distearate Aluminum Sulfate, Aluminum Dimyristate, Aluminum Calcium Sodium Silicate and Aluminum Citrate. Of course, it is contemplated that these salts are not the only salts that can be added to the emulsions.

Example Product Forms

As is apparent by comparing the three formulation examples of Table 1, a wide range of different emulsion systems with different consumer benefits can be realized.

1. Antiperspirant Cream or Spray Lotion

In one particular embodiment, the water-in-silicone lotion can be an anti-perspirant cream or sprayable lotion. In addition to containing active ingredients from the OTC Anti-Perspirant Monograph (published by the U.S. Food and Drug Administration), other compounds may be added. For example, water soluble actives such as ammonium alum and aluminum citrate may be added in the water phase. Other water soluble actives that may be added include peptides which exhibit botox-like activity, and PCMs such as Lauric Acid and Myristic Acid. Additional actives such as the following aluminum compounds may be added to the formulation: sodium aluminum phosphate, aluminum stearate, aluminum calcium sodium silicate and/or aluminum dimyristate.

2. Skin Barrier Spray

In another embodiment, the formulation is a sprayable that can be used to prevent diaper rash. While providing excellent efficacy, typical diaper rash creams are difficult to apply, have poor aesthetics and are messy upon application. The present disclosure would allow delivery of a high load of Dimethicone, an OTC Skin Protectant with a silky or powdery skin feel, in a convenient spray application.

3. Moisturizing Body Cream

In another embodiment, the formulation is a moisturizing body cream that contains glycerin to help moisturize the skin and a high level of silicone oils to ensure ease of application and present after-feel for the user.

TABLE 1

| | Anti-Sweat Spray Formulation 1 | Skin Barrier Spray Formulation 2 | Moisturizing Body Cream Formulation 3 |
|---|---|---|---|
| Part A | | | |
| Water* | 14.5 | 40.5 | 67.5 |
| Butylene Glycol | 5 | 5 | 0 |
| Glycerin | 0 | 0 | 5 |
| Ammonium Alum | 5 | 0 | 0 |
| Aluminum Citrate | 1 | 1 | 0 |
| Sodium Chloride | 0 | 0 | 3 |
| Sodium Hydroxide (20%) | 7 | 0 | 0 |
| Zinc Chloride | 0 | 2 | 0 |
| Xanthan Gum* | 0.2 | 0.2 | 0.2 |
| Chlorphenesin* | 0.1 | 0.1 | 0.1 |
| Methylparaben* | 0.2 | 0.2 | 0.2 |
| Part B | | | |
| Aldoxia | 2 | 0 | 0 |
| Aluminum Stearate | 1 | 0 | 0 |
| Beadyl Beads | 1 | 0 | 0 |
| J-24-MT | 1 | 0 | 0 |
| Dimethicone (2 cst) | 10 | 0 | 10 |
| Dimethicone (10 cst)* | 20 | 30 | 10 |
| Dimethicone (1000 cst) | 1 | 0 | 1 |
| SILUBE J1015-0-812* (Lauryl PEG/PPG-18/18 Dimethicone) | 10 | 10 | 2 |
| BENTONE Gel CAO* (Stearalkonium Hectorite) | 10 | 10 | 1 |
| Lauric Acid | 6.6 | 0 | 0 |
| Myristic Acid | 3.4 | 0 | 0 |
| Part C (OPTIONAL) | | | |
| XIAMETER PMX-200 Silicone Fluid 0.65 cst* | 1 | 1 | 1 |

*ingredient common to all product forms

EXPERIMENTAL DATA

The procedure for making the water-in-oil emulsion of the current disclosure for Experiments 1, 2 and 3 has the following steps:

1) Prehydrate the xanthan gum with glycerin (this step only applies to Experiments 1 and 2).
2) Add all ingredients of Part A (water phase) into a beaker and heat to 75° C.
3) Add all ingredients of Part B (oil phase) into a beaker and heat to 75° C.
4) Slowly add Part A to Part B while homogenizing using a Silverson homogenizer at 5000 rpm for 5 minutes. Addition of the water to the oil phase should be done at a rate such that very little or no free water is observed during the homogenization process.
5) Cool the resulting emulsion to room temperature.
6) Package the emulsion into 2 ounce jars for stability testing.
7) Place the 2 ounce jars for each sample in an environment of 40° C. for 90 days.

8) After 90 days, observe the jars for separation between the oil and water phase.

Experiment 1

This experiment was performed with three different emulsions having 60.5% water content (by weight). As shown below, the ratio of lauryl PEG/PPG-18/18 dimethicone to stearalkonium hectorite is sensitive. Surprisingly, only the 1:1 ratio was stable after the stability testing was performed. A slight variance either way resulted in an unstable emulsion.

TABLE 2

|  | Unstable 1 Weight % | STABLE 2 Weight % | Unstable 3 Weight % |
|---|---|---|---|
| Part A |  |  |  |
| Water | 60.5 | 60.5 | 60.5 |
| Glycerin | 5 | 5 | 5 |
| Sodium Chloride | 3 | 3 | 3 |
| Xanthan Gum | 0.2 | 0.2 | 0.2 |
| Chlorphenesin | 0.1 | 0.1 | 0.1 |
| Methylparaben | 0.2 | 0.2 | 0.2 |
| Part B |  |  |  |
| Dimethicone (2 cst) | 10 | 10 | 10 |
| Dimethicone (10 cst) | 10 | 10 | 10 |
| Dimethicone (1000 cst) | 1 | 1 | 1 |
| Lauryl PEG/PPG-18/18 Dimethicone | 6 | 5 | 4 |
| Stearalkonium Hectorite | 4 | 5 | 6 |
|  | 100 | 100 | 100 |

Experiment 2

This experiment was performed with emulsions having 65.5% or 67.5% water content (by weight). As shown below, the ratio of lauryl PEG/PPG-18/18 dimethicone to stearalkonium hectorite is sensitive. Surprisingly, at such a high water content, only the 2:1 ratio was stable after the stability testing was performed.

TABLE 3

|  | Unstable 4 Weight % | Unstable 5 Weight % | Unstable 6 Weight % | STABLE 7 Weight % |
|---|---|---|---|---|
| Part A |  |  |  |  |
| Water | 65.5 | 65.5 | 67.5 | 67.5 |
| Glycerin | 5 | 5 | 5 | 5 |
| Sodium Chloride | 3 | 3 | 3 | 3 |
| Xanthan Gum | 0.2 | 0.2 | 0.2 | 0.2 |
| Chlorphenesin | 0.1 | 0.1 | 0.1 | 0.1 |
| Methylparaben | 0.2 | 0.2 | 0.2 | 0.2 |
| Part B |  |  |  |  |
| Dimethicone (2 cst) | 10 | 10 | 10 | 10 |
| Dimethicone (10 cst) | 10 | 10 | 10 | 10 |
| Dimethicone (1000 cst) | 1 | 1 | 1 | 1 |

TABLE 3-continued

|  | Unstable 4 Weight % | Unstable 5 Weight % | Unstable 6 Weight % | STABLE 7 Weight % |
|---|---|---|---|---|
| Lauryl PEG/PPG-18/18 Dimethicone | 4 | 1 | 1.5 | 2 |
| Stearalkonium Hectorite | 1 | 4 | 1.5 | 1 |
|  | 100 | 100 | 100 | 100 |

Experiment 3

Evaluation of Rheology Modifiers and Gelling Agents

Prior to discovering the effectiveness of Lauryl PEG/PPG-18/18 Dimethicone, many different types of emulsifying surfactants were evaluated and failed to produce an emulsion which remained stable overnight. The base formulation used to evaluate these emulsifiers is provided below in addition to the emulsifiers which failed to provide a stable emulsion.

TABLE 4

| Trade Name | Vendor | INCI Name | Weight % |
|---|---|---|---|
| Part A |  |  |  |
| Water | N/A | Water | 10.2 |
| Butylene Glycol CULINOX 99 | Oxea Corporation Culinox | Butylene Glycol Sodium Chloride | 5 1 |
| TIC Prehydrated Xanthan Gum | TIC Gums | Xanthan Gum | 0.1 |
| Part B |  |  |  |
| XIAMETER PMX-200 SILICONE FLUID 10 CS | Dow Corning | Dimethicone | 63.7 |
| Lauric Acid PC Emulsifier | Protameen N/A | Lauric Acid N/A | 10 10 |

The following emulsifiers were evaluated for their ability to form stable emulsions: from Evonik Industries (Essen, Germany): ABIL® WE 09 (Polyglyceryl-4 Isostearate and Cetyl PEG/PPG-10/1 Dimethicone and Hexyl Laurate); ABIL® EM 90 (Cetyl PEG/PPG-10/1 Dimethicone); ISOLAN® PDI (Diisostearoyl Polyglyceryl-3 Dimer Dilinoleate); and ABIL® EM 97 (Bis-PEG/PPG-14/14 Dimethicone and Dimethicone). From Inolex (Philadelphia, Pa.): EMULSIL® WO-3115 (Cyclotetrasiloxane (and) Cyclopentasiloxane (and) PEG/PPG-18/18 Dimethiconol). From Grant Industries, Inc (Elmwood Park, N.J.): GRANSURF 67 (PEG-10 Dimethicone); GRANSURF 90 (Cetyl PEG/PPG-10/1 Dimethicone); GRANSURF NR-WO (Cyclopentasiloxane (and) PEG-10 dimethicone (and) bentonite (and) distearyldimonium Chloride); and GRANSURF W9 (Cetyl PEG/PPG-10/1 Dimethicone (and) Hexyl Laurate (and) Polyglyceryl-4. Isostearate). From Shin-Etsu Chemical Company, Ltd. (Toyko, Japan): KF-6050L (DIMETHICONE (AND) PEG/PPG-18/18 DIMETHICONE); KF-6038 (Lauryl PEG-9 Polymethylsiloxyethyl Dimethicone); KSG-210 (Dimethicone and Dimethicone/PEG-10/15 Crosspolymer); and KF-6017 (PEG-10 Dimethicone). From Momentive Performance Materials, Inc. (Waterford, N.Y.): SF1328 (Cyclomethicone and PEG/PPG-20/15 Dimethicone). From Siltech Corporation (Toronto, Canada):

SILUBE® T308-16 (Cetyl PEG/PPG-10/1 Dimethicone); SILSURF® 400R (Cyclopentasiloxane and PEG/PPG-18/18 Dimethicone). From Jeen® International Corporation (Fairfiled, N.J.): JEESILC DMC-522 (Cyclopentasiloxane (and) PEG/PPG-18/18 Dimethicone); JEESILC EM520 (LAURYL PEG/PPG-18/18 METHICONE); and JEESILC IDD (Isododecane (and) Dimethicone and Crosspolymer-3). From Clariant International Ltd., (Muttenz, Switzerland): SILCARE® Silicone WSi (Amodimethicone Glycerocarbamate). From Dow Corning (Midland, Mich.): FZ-2233 (Bis-Isobutyl PEG/PPG-10/7/Dimethicone Copolymer); and ES-5612 FORMULATION AID (PEG-10 Dimethicone). Emulsifying agents which were able to temporarily stabilize the emulsion included KF-6050L (Dimethicone, PEG/PPG-18/18 Dimethicone), SF1328 (Cyclomethicone and PEG/PPG-20/15 Dimethicone), JEESILC DMC 522 (Cyclopentasiloxane, PEG/PPG-18/18 Dimethicone) and SILUBE J1015-O-812 (Lauryl PEG/PPG-18/18 Dimethicone). However, the presence of these emulsifiers alone was not sufficient to ensure adequate or long-term physical stability.

The following gelling agents and other rheology modifiers were added at 10% to the base formulation containing one of the four emulsifiers (concentration still at 10%). Overall, the goal was to provide sufficient viscosity and emulsion stability while still maintaining a viscosity low enough to spray.

The following components were evaluated for stability. From Evonik Industries (Essen, Germany) ABIL CARE 180 (Cetyl PEG/PPG-10/1 Dimethicone). From Elementis Specialties (London, England) BENTONE GEL ISD V (Isododecane, Disteardimonium Hectorite, Propylene Carbonate), BENTONE GEL PTIS V (Pentaerythrityl Tetraisostearate, Disteardimonium, Hectorite, Propylene Carbonate), BENTONE GEL 1002 V (Cyclopentasiloxane, Disteardimonium Hectorite, Propylene Carbonate), BENTONE GEL CAO V (Ricinus Communis (Castor) Seed Oil, Stearalkonium Hectorite, Propylene Carbonate), BENTONE GEL OMS V (C11-12 Isoparaffin, Disteardimonium Hectorite, Alcohol Denat.), BENTONE GEL VS5-PC V (Cyclomethicone, Disteardimonium Hectorite, SD Alcohol 40), BENTONE SD-1 (N/A organic derivative of a bentonite clay), BENTONE 27V CG (Stearalkonium Hectorite), BENTONE 38 V (Disteardimonium Hectorite). From Chemisil Silicones, Inc. (Chatsworth, Calif.): CHEMSIL K-12 (Dimethicone and Dimethicone/PEG-10/15 Crosspolymer), CHEMSIL K-13 (Cyclopentasiloxane and Dimethicone/Vinyl Dimethicone Crosspolymer), CHEMSIL K-50 (Isododecane (and) Acrylate/Dimethicone Copolymer), CHEMSIL K-51 (Cyclopentasiloxane and Dimethicone/Vinyl Dimethicone Crosspolymer), GELAID CPE (Cyclopentasiloxane, Dimethicone/Vinyl Dimethicone Crosspolymer, Hydroxyethy Acrylate, Sodium Acryloyl Dimethyl Taurate Copolymer, Cyclohexasiloxane). From BK Giulini GmbH (Ludwigshafen, Germany): GILUGEL CAO (Ricinus Communis (Castor) Seed Oil, Aluminum/Magnesium Hydroxide Stearate). From Grant Industries, Inc. (Elmwood Park, N.J.): GRANSIL DMG-2 (Dimethicone (and) Polysilicone-11), GRANSIL GTS (Polysilicone-11, Stearoxymethicone/Dimethicone Copolymer), GRANSIL GVL (Coconut Alkanes (and) Polysilicone-11), GRANSIL 50C-HM (Dimethicone (and) PEG/PPG-18/18 Dimethicone), GRANSIL IDS-5 (Isododecane. Cyclopentasiloxane, Polysilicone-11), GRANSIL PC-12 (Isododecane, Polysilicone-11), GRANSIL PC-12P (Isododecane, Polyethylene, Polysilicone-11). From Jeen International Corporation (Fairfiled, N.J.): JEELUX V2T (Isododecane, Triisostearyl Citrate and Bis-Vinyl Dimethicone/Dimethicone Copolymer), JEELUX D2T (Isohexadecane, Dimethicone, Triisostearyl Citrate, Bis-Vinyl Dimethicone/Dimethicone Copolymer). From Siltech Corporation (Toronto, Canada): SILMER G-162 (Dimethicone/Vinyl Dimethicone Crosspolymer), SILWAX D226 (Cerotyl Dimethicone), SILWAX Di-5026 (Cerotyl Dimethicone), SILWAX H416 (Cetyl Dimethicone), SILWAX S (Dimethiconol Stearate). From Cremer Oleo GmbH & Co. KG (Hamburg, Germany): SOFITSAN Gel (Bis-Diglyceryl Polyacyladipate-1, Propylene Glycol Dicaprylate/Dicaprate, Stearalkonium Hectorite, Propylene Carbonate).

The resulting formulations were visually assessed as to whether phase separation or free oil droplets were observed throughout the 3-month stability assessment. Viscosity measurements were obtained using a Brookfield LV IV Viscometer (spindle 65, 10 rpm).

Of the rheology modifiers evaluated, only those containing Stearalkonium Hectorite were found to create a stable, low-viscosity water-in-silicone emulsion that is largely anhydrous when combined with Lauryl PEG/PPG-18/18 Dimethicone (SILUBE J1015-O-812). Surprisingly, not even gelling agents containing Disteardimonium Hectorite, chemically very similar to Stearalkonium Hectorite, were able to produce stable emulsions. Removal of the Lauryl PEG/PPG-18/18 Dimethicone resulted in a loss of physical stability.

EMBODIMENTS

Embodiment 1

A cosmetic emulsion comprising: a water phase comprising about 10% to about 67.5% water by total weight of the cosmetic emulsion; and an oil phase comprising: (a) stearalkonium hectorite; and (b) a silicone alkyl polyether selected from the group consisting of: PEG/PPG-18/18 dimethicone, PEG/PPG-20/15 dimethicone, and Lauryl PEG/PPG-18/18 dimethicone.

Embodiment 2

The cosmetic emulsion of embodiment 1, wherein the silicone alkyl polyether is Lauryl PEG/PPG-18/18 dimethicone.

Embodiment 3

The cosmetic emulsion of embodiment 2, wherein a ratio of the Lauryl PEG/PPG-18/18 dimethicone to the stearalkonium hectorite ranges from 1:3 to 3:1.

Embodiment 4

The cosmetic emulsion of embodiment 1 or embodiment 2, wherein a ratio of the silicone alkyl polyether to the stearalkonium hectorite is at least 1:1.

Embodiment 5

The cosmetic emulsion of embodiment 4, wherein the ratio of the silicone alkyl polyether to the stearalkonium hectorite is less than 2:1.

Embodiment 6

The cosmetic emulsion of any one of the preceding embodiments, wherein a total concentration of the stearalkonium hectorite and the silicone alkyl polyether is 20% or less by total weight of the cosmetic emulsion.

Embodiment 7

The cosmetic emulsion of any one of the preceding embodiments, wherein the oil phase further comprises a silicone oil.

Embodiment 8

The cosmetic emulsion of any one of the preceding embodiments, wherein the cosmetic emulsion is sprayable.

Embodiment 9

A cosmetic emulsion comprising: a water phase comprising about 10% to about 45% water by total weight of the cosmetic emulsion; and an oil phase comprising: (a) stearalkonium hectorite; and (b) a silicone alkyl polyether selected from the group consisting of: PEG/PPG-18/18 dimethicone, PEG/PPG-20/15 dimethicone, and Lauryl PEG/PPG-18/18 dimethicone; and wherein the cosmetic emulsion is sprayable.

Embodiment 10

The cosmetic emulsion of embodiment 9, wherein the silicone alkyl polyether is Lauryl PEG/PPG-18/18 dimethicone.

Embodiment 11

The cosmetic emulsion of embodiment 10, wherein a ratio of the Lauryl PEG/PPG-18/18 dimethicone to the stearalkonium hectorite ranges from 1:3 to 3:1.

Embodiment 12

The cosmetic emulsion of embodiment 9 or 10, wherein a ratio of the silicone alkyl polyether to the stearalkonium hectorite is at least 1:1.

Embodiment 13

The cosmetic emulsion of embodiment 12, wherein the ratio of the silicone alkyl polyether to the stearalkonium hectorite is less than 2:1.

Embodiment 14

The cosmetic emulsion of any one of embodiments 9-13, wherein a total concentration of the stearalkonium hectorite and the silicone alkyl polyether is 20% or less by total weight of the cosmetic emulsion.

Embodiment 15

The cosmetic emulsion of any one of embodiments 9-14, wherein the oil phase further comprises a silicone oil.

Embodiment 16

A cosmetic emulsion in a form of a lotion or cream, the cosmetic emulsion comprising: a water phase comprising about 45% to about 67.5% water (by total weight of the emulsion); and an oil phase comprising: (a) stearalkonium hectorite; and (b) a silicone alkyl polyether selected from the group consisting of: PEG/PPG-18/18 dimethicone, PEG/PPG-20/15 dimethicone, and Lauryl PEG/PPG-18/18 dimethicone.

Embodiment 17

The cosmetic emulsion of embodiment 16, wherein the silicone alkyl polyether is Lauryl PEG/PPG-18/18 dimethicone.

Embodiment 18

The cosmetic emulsion of embodiment 17, wherein a ratio of the Lauryl PEG/PPG-18/18 dimethicone to the stearalkonium hectorite ranges from 1:3 to 3:1.

Embodiment 19

The cosmetic emulsion of any one of embodiments 16-18, wherein the ratio of the silicone alkyl polyether to the stearalkonium hectorite is 2:1.

Embodiment 20

The cosmetic emulsion of any one of the preceding embodiments, wherein the oil phase further comprises a phase change material.

Embodiment 21

The cosmetic emulsion of embodiment 20, wherein the phase change material is a combination of lauric acid and myristic acid.

Embodiment 22

The cosmetic emulsion of any one of the preceding embodiments, further comprising: an aluminum salt, the aluminum salt ranging from 0.25% to 1.0% aluminum content.

Embodiment 23

The cosmetic emulsion of embodiment 22, wherein the aluminum salt is selected from the group consisting of: Ammonium and Potassium Alum, Aluminum Triphosphate, Sodium aluminum Phosphate, Aldioxa, Aluminum Stearate, Aluminum Distearate Aluminum Sulfate, Aluminum Dimyristate, Aluminum Calcium Sodium Silicate and Aluminum Citrate.

When introducing elements of the present disclosure or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements. Many modifications and variations of the present disclosure can be made without departing from the spirit and scope thereof. Therefore, the exemplary embodiments described above should not be used to limit the scope of the invention.

What is claimed is:
1. A cosmetic emulsion comprising:
a water phase comprising an amount of water, the amount of water being less than 65.5% by total weight of the cosmetic emulsion; and an oil phase comprising:
- (a) stearalkonium hectorite; and
- (b) a silicone alkyl polyether selected from the group consisting of: PEG/PPG-18/18 dimethicone, PEG/PPG-20/15 dimethicone, and Lauryl PEG/PPG-18/18 dimethicone; wherein a total concentration of the stearalkonium hectorite and the silicone alkyl polyether is 20% or less by total weight of the cosmetic emulsion; wherein a ratio between the stearalkonium hectorite to the silicone alkyl polyether ranges from 1:3 to 3:1;

wherein the cosmetic emulsion is sprayable, and wherein the amount of water and the ratio between the stearalkonium hectorite to the silicone alkyl polyether results in the cosmetic emulsion being stable.

2. The cosmetic emulsion of claim 1, wherein the silicone alkyl polyether is Lauryl PEG/PPG-18/18 dimethicone.

3. The cosmetic emulsion of claim 1, wherein the oil phase further comprises a silicone oil.

4. The cosmetic emulsion of claim 1, wherein the ratio between the stearalkonium hectorite to the silicone alkyl polyether is 1:1.

5. The cosmetic emulsion of claim 4, wherein the silicone alkyl polyether is Lauryl PEG/PPG-18/18 dimethicone.

6. A cosmetic emulsion in a form of a lotion or cream, the cosmetic emulsion comprising:

a water phase comprising an amount of water, the amount of water being at least 65.5% (by total weight of the emulsion); and an oil phase comprising:
- (a) stearalkonium hectorite; and
- (b) a silicone alkyl polyether selected from the group consisting of: PEG/PPG-18/18 dimethicone, PEG/PPG-20/15 dimethicone, and Lauryl PEG/PPG-18/18 dimethicone; wherein a total concentration of the stearalkonium hectorite and the silicone alkyl polyether is 20% or less by total weight of the cosmetic emulsion; wherein a ratio between the stearalkonium hectorite and the silicone alkyl polyether ranges from 1:3 to 3:1;
- and wherein the amount of water and the ratio between the stearalkonium hectorite to the silicone alkyl polyether results in the cosmetic emulsion being stable.

7. The cosmetic emulsion of claim 6, wherein the silicone alkyl polyether is Lauryl PEG/PPG-18/18 dimethicone.

8. The cosmetic emulsion of claim 6, wherein the ratio of the silicone alkyl polyether to the stearalkonium hectorite is 2:1.

9. The cosmetic emulsion of claim 8, wherein the silicone alkyl polyether is Lauryl PEG/PPG-18/18 dimethicone.

* * * * *